US009566399B1

(12) United States Patent
Bono et al.

(10) Patent No.: US 9,566,399 B1
(45) Date of Patent: Feb. 14, 2017

(54) DEEP LUNG ALVEOLAR AEROSOL TARGETED DRUG DELIVERY

(71) Applicants: Michael Bono, Collegeville, PA (US); William Clementi, Rosemont, PA (US)

(72) Inventors: Michael Bono, Collegeville, PA (US); William Clementi, Rosemont, PA (US)

(73) Assignee: Clempharma LLC, Rosemont, PA (US)

( * ) Notice: Subject to any disclaimer, the term of this patent is extended or adjusted under 35 U.S.C. 154(b) by 0 days.

(21) Appl. No.: 15/093,812

(22) Filed: Apr. 8, 2016

Related U.S. Application Data (63) Continuation-in-part of application No. 14/686,232, filed on Apr. 14, 2015, now abandoned.

(51) Int. Cl.
*A61M 11/00* (2006.01)
*A61M 15/00* (2006.01)
*A61M 11/02* (2006.01)

(52) U.S. Cl.
CPC ............ *A61M 11/003* (2014.02); *A61M 11/02* (2013.01); *A61M 15/0021* (2014.02); *A61M 15/0086* (2013.01); *A61M 2205/586* (2013.01)

(58) Field of Classification Search
None
See application file for complete search history.

(56) References Cited

U.S. PATENT DOCUMENTS

| 3,301,255 A | 1/1967 | Thompson |
| 4,094,317 A | 6/1978 | Wasnich |
| 4,674,491 A * | 6/1987 | Brugger ................. A61M 11/06 128/200.14 |
| 4,741,331 A * | 5/1988 | Wunderlich .......... A61M 15/02 128/200.15 |
| 5,086,765 A * | 2/1992 | Levine .................. A61M 15/00 128/200.14 |
| 5,170,782 A | 12/1992 | Kocinski |
| 5,234,907 A | 8/1993 | Bolin |

(Continued)

FOREIGN PATENT DOCUMENTS

WO    WO2007/145866    12/2007

OTHER PUBLICATIONS

Google search—"high density" aerosol aviptadil (results attached).*

(Continued)

*Primary Examiner* — Tan-Uyen (Jackie) T Ho
*Assistant Examiner* — Joseph D Boecker
(74) *Attorney, Agent, or Firm* — Joseph E. Maenner; Petock & Petock, LLC (57) ABSTRACT

An aerosol inhalation device assembly for diagnostic and therapeutic use for deep lung alveolar aerosol targeted drug delivery includes a nebulizer for generating an aerosol containing droplets of a liquid. The nebulizer has a pressurized gas inlet and a nebulizer outlet. An inhalation chamber is in fluid communication with the nebulizer outlet. The inhalation chamber is defined by at least one sidewall. An inhalation mouthpiece assembly is in fluid communication with the inhalation chamber and extends outwardly from the at least one sidewall of the inhalation chamber. A filter assembly is in fluid communication with the inhalation chamber. The filter assembly includes a filter medium. An exit port is in direct fluid communication with the filter assembly. A method of using the nebulizer is also provided.

18 Claims, 5 Drawing Sheets

(56) References Cited

U.S. PATENT DOCUMENTS

| | | | |
|---|---|---|---|
| 5,235,969 A | | 8/1993 | Bellm |
| 5,318,015 A | * | 6/1994 | Mansson ............ A61M 15/0065 128/200.21 |
| 5,355,872 A | | 10/1994 | Riggs et al. |
| 5,603,314 A | * | 2/1997 | Bono ...................... A61M 11/06 128/200.14 |
| 5,611,332 A | | 3/1997 | Bono |
| 5,630,409 A | | 5/1997 | Bono et al. |
| 5,960,792 A | * | 10/1999 | Lloyd ............... A61M 15/0045 128/200.14 |
| 5,996,576 A | * | 12/1999 | Yule ...................... B05B 7/0807 128/203.12 |
| 6,129,080 A | * | 10/2000 | Pitcher .................. A61M 11/06 128/200.14 |
| 6,230,703 B1 | * | 5/2001 | Bono ...................... A61M 11/06 128/200.14 |
| 6,328,030 B1 | | 12/2001 | Kidwell et al. |
| 6,412,481 B1 | * | 7/2002 | Bienvenu .......... A61M 15/0086 128/200.21 |
| 6,450,163 B1 | | 9/2002 | Blacker et al. |
| 6,551,578 B2 | | 4/2003 | Adjei et al. |
| 6,644,304 B2 | | 11/2003 | Grychowski et al. |
| 6,660,715 B2 | | 12/2003 | Klibanov |
| 6,705,316 B2 | | 3/2004 | Blythe et al. |
| 6,883,517 B2 | | 4/2005 | Halamish |
| 6,997,184 B2 | | 2/2006 | Donohue |
| 7,037,252 B2 | | 5/2006 | Flanagan et al. |
| 7,267,120 B2 | | 9/2007 | Rustad et al. |
| RE40,591 E | | 12/2008 | Denyer |
| 7,559,322 B2 | | 7/2009 | Foley et al. |
| 7,568,480 B2 | | 8/2009 | Foley et al. |
| 7,571,722 B2 | | 8/2009 | Wuttke et al. |
| 7,634,995 B2 | | 12/2009 | Grychowski et al. |
| 7,819,115 B2 | | 10/2010 | Sexton et al. |
| 7,900,625 B2 | | 3/2011 | Kleinstreuer et al. |
| 7,905,228 B2 | | 3/2011 | Blacker et al. |
| 7,954,487 B2 | | 6/2011 | Grychowski et al. |
| 7,958,891 B2 | | 6/2011 | Smith et al. |
| RE42,911 E | | 11/2011 | Denyer |
| 8,061,352 B2 | | 11/2011 | Grychowski et al. |
| 8,267,081 B2 | | 9/2012 | Flanagan et al. |
| 8,397,712 B2 | | 3/2013 | Foley et al. |
| 8,459,252 B2 | | 6/2013 | Gallem et al. |
| 8,561,607 B2 | | 10/2013 | Cortez, Jr. et al. |
| 8,596,264 B2 | * | 12/2013 | Sommer ................ A61M 11/06 128/200.14 |
| RE45,068 E | | 8/2014 | Schmidt et al. |
| 2002/0128206 A1 | | 9/2002 | Hay et al. |
| 2003/0005929 A1 | * | 1/2003 | Grychowski .......... A61M 11/06 128/203.12 |
| 2008/0054099 A1 | | 3/2008 | Giroux et al. |
| 2008/0066741 A1 | | 3/2008 | LeMahieu et al. |
| 2011/0108025 A1 | | 5/2011 | Fink et al. |
| 2011/0253134 A1 | * | 10/2011 | Chen ...................... A61M 11/06 128/200.23 |
| 2014/0230811 A1 | * | 8/2014 | Von Hollen ........... A61M 11/06 128/200.14 |

OTHER PUBLICATIONS

Google search—"high density" aerosol vasoactive (results attached).*
Google search—optimal aerosol density for deep lung (results attached).*
Email communication between the Division of Industry and Consumer Education (DICE) at FDA's Center for Devices and Radiological Health (CDRH).*
"Discovery Labs Announces Presentation & Key Results of Phase 2a Study of Aerosolized KL4 Surfactant in Cystic Fibrosis at the North American Cystic Fibrosis Conference", Drugs.com, Oct. 22, 2010. 3 pages.
"Inhaled Doxorubicin in Phase I Lung Cancer Trial", Primary Care & Cancer, vol. 2, No. 10 (Nov./Dec. 2000). 1 page.
Usmani, Omar S. et al., "Regional Lung Deposition and Bronchodilator Response as a Function of Beta2 Agonist Particle Size", pp. 1497-1504.
Labiris, N.R. et al., "Pulmonary drug delivery. Part II: The role of inhalant delivery devices and drug formulations in therapeutic effectiveness of aerosolized medications", Clinical Pharmacal, 56, Apr. 18, 2002, pp. 600-612.
Labiris, N.R. et al., "Pulmonary drug delivery. Part I: The role of inhalant delivery devices and drug formulations in therapeutic effectiveness of aerosolized medications", Clinical Pharmacal, 56, Apr. 19, 2002, pp. 588-599.
Usmani, Omar S., "Small-airway disease in asthma: pharmacological considerations", Curr. Pulm. Med., 21: pp. 55-67, 2015.
Biddiscombe, Martin F. et al., "Comparing Lung Regions of Interest in Gamma Scintigraphy for Assessing Inhaled Therapeutic Aerosol Deposition", Journal of aerosol Medicine and Pulmonary Drug Delivery, vol. 24, No. 3, 2011, pp. 165-173.
Zhou, Qi, et al., "Inhaled Formulations and pulmonary drug delivery systems for respiratory infections", Advanced Drug Delivery Review, 2014, 17 pages.
Flume, Patrick A. et al., "Clinical applications of pulmonary delivery of antibiotics", Advanced Drug Delivery Review, 2014, 6 pages.
Mayosky, C. et al., "99mTc-ENS vs. 99mTc-DTPA as Aerosol Lung Scintiscanning Agents", Alasbimn Journal 6(24): Apr. 2004. Article No. AJ24-3. 5 pages.
Stein, Evan, et al. "Success of a Safe and Simple Algorithm to Reduce Use of CT Pulmonary Angiography in the Emergency Department", AJR:194, Feb. 2010, pp. 392-397.
Suskind, Herbert, "Inhalation Delivery of Drugs", The Journal of Nuclear Medicine, vol. 38, No. 9, Sep. 1997, p. 1065.
Freeman, Leonard M., "Don't Bury the V/Q Scan: Its as Good as Multidetector CT Angiograms wirth a Lot Less Radiation Exposure", Society of Nuclear Medicine, vol. 49, No. 1, Jan. 2008, pp. 5-8.
Guan L. et al. "Validation of hyperpolarized helium-3 MR imaging for measurement of regional ventilation/perfusion with radionuclide techniques", Hospital of the University of Pennsylvania, undated. 4 pages.
Sankagiri N., et al. "Evaluation and Design of Nebulizers for Nuclear Medicine Diagnostics" ILASS Americas, 11th Annual Conference on Liquid Atomization and Spray Systems, Sacramento, CA May 1998. 5 pages.
Ostrander, Kevin D. et al., "Potential Deep Lung Delivery of Water-Insoluble Drug Nanocrystals Via the AMICI Swirler Nebulizer System", undated. 8 pages.
Carter, N.J., et al., "Evaluating the Swirler nebulizer: A user's perspective", Nuclear Medicine Communications, 1998, 19, pp. 599-604.
Ishii, Masaru et al., "Hyperpolarized helium-3 MR imaging of pulmonary function", Radiol Clin N Am 43 (2005), pp. 235-246.
Eustance, Cedric, "Lung Scanning with Microaerosols", undated. 5 pages.
Robb, Matthew, "Like One Hundred X-rays? Study Suggests Many Referring Physicians Don't Grasp or Explain to Patients the Radiation Exposure Involved with CT", Radiology Today, Jul. 2004. 1 page.
Office Action for U.S. Appl. No. 14/686,232, mailed Jul. 16, 2015.
Final Office Action for U.S. Appl. No. 14/686,232, mailed.
Advisory Action for U.S. Appl. No. 14/686,232, mailed Feb. 24, 2016.
Leuchte et al., "Inhalation of vasoactive intestinal peptide in pulmonary hypertension", Eur Respir J 2008; 32: 1289-1294.
Saga et al., "Vasoactive intestinal peptide relaxes isolated strips of human bronchus, pulmonary artery, and lung parenchyma", Trans Assoc. Am Physicians. 1984; 97:304-10 (Abstract only provided).
Barnes et al., "The effect of inhaled vasoactive intestinal peptide on bronchial reactivity to histamine in humans", Am Rev Respir Dis. Aug. 1984; 130(2): 162-6 (Abstract only provided).
Kejizers G.B., "Aviptadel (Senatek)", Curr Opin Investig Drugs. Apr. 2001; 2(4):545-9 (Abstract only provided).

* cited by examiner

DEEP LUNG ALVEOLAR AEROSOL TARGETED DRUG DELIVERY

CROSS-REFERENCE TO RELATED APPLICATIONS

The present application is a Continuation-in-Part application of U.S. patent application Ser. No. 14/686,232, filed Apr. 14, 2015, which is incorporated herein by reference in its entirety. Also, the teachings of U.S. Pat. No. 5,603,314, issued on Feb. 18, 1997, U.S. Pat. No. 5,611,332, issued on Mar. 18, 1997, U.S. Pat. No. 5,630,409, issued on May 20, 1997, and U.S. Pat. No. 6,230,703, issued on May 15, 2001, are all incorporated herein by reference.

BACKGROUND OF THE INVENTION

Field of the Invention

The present invention relates to a drug and device combination, and, in particular, to a drug and device combination for administering an aerosolized medication to the lungs.

Description of the Related Art

Aerosol inhalation equipment such as nebulizers are often used in medical facilities for generating aerosol mists for diagnostic and therapeutic procedures. The mists can originate from liquids, suspensions, colloids, nano-colloids or nano- or micronized dry powders. Historically, these devices were solely used in hospitals but now some can be used in the home and include Metered Dose Inhalers (MDIs for patients with asthma or re-current bronchospasm.) Some patients with asthma, especially during severe episodes, do require nebulizer treatment at home but these devices are cumbersome and "continuous medication feed" therapy is not presently available in the home care setting.

Whether in the home or hospital, a metered dose is important because the therapeutic agents delivered (bronchodilators in asthma to congestive heart failure drugs such as VIP) are highly active biologically and dose must be controlled to impart precision and titration in the therapeutic or clinical effect seen especially when the patient is in home care setting. Such devices are especially useful, such as, for example, in pulmonary therapy for severe bronchospasm as in asthma, infectious diseases such as pneumonia (bacterial or fungal including *Mycobacterium tuberculae*), and vasodilators of the venous circulation systemically or within the pulmonary tree. They may be useful for introducing radioactive vapors or for special receptor binding agents used for diagnosing diseases. Typically, when devices have been developed for diagnostic use with radioactive materials, they are not used for therapeutic use because diagnostic devices require special handling, lead encasement for example, and a complex design compatible with safe uses of radioactive material. Diagnostic devices are typically designed for single application in hospitals or other medical facilities, where the use can be controlled. Diagnostic devices must prevent radioactive contamination to other caregivers and patients and in the physical area of treatment (room or corridor), and therefore route expelled air through a filter to prevent radioactive particles from exiting the device into the atmosphere. A key difference between diagnostic devices and drug delivery nebulizers is that the exhaled air path in drug delivery nebulizers is not controlled for drug delivery devices; while the purpose of controlling air flow in diagnostic radioactive agent delivery is to reduce contamination but not to optimize drug delivery. Another key difference is that residual volume can be higher than expected in diagnostic devices because the diagnostic devices are single use devices containing radioactive substances and therefore must be disposed immediately after use or within 30 minutes after the diagnostic procedure is complete, whereas drug delivery nebulizers can be reused.

To date, aerosol drug delivery has focused on pressurized cans or metered inhalers. Nebulizers used with an air pump have typically only been used for severe acute exacerbations of symptoms or where bronchospasm makes inspiration difficult. For conditions where expiration is reduced or restricted such as in asthma acutely and in chronic obstructive pulmonary disease ("COPD") or emphysema, nebulizers are used acutely but over a longer period than one or two puffs used to relieve symptoms of asthma. In some cases, the nebulizers maybe used from minutes to hours until blood oxygen returns to normal and remains at normal levels. Especially in these cases where blood oxygen has fallen, the inhaled vapor should contain a "high payload of drug" per inspired breath to achieve the desired therapeutic effect. Delivering drugs under low-pressure conditions, by contrast, is difficult, patient pulmonary status dependent, and maybe ineffective. MDIs develop pressures up to 50 pounds per square inch upon exit at the nozzle ("psi") to be effective and are in part dependent of the inhalation pressure or inspiration "vacuum" generated by the patient. Because inhalation pressure is low upon inhalation via a spacer for example and is dependent on the patient's lung capacity, parameters such as droplet size for aqueous and/or non-aqueous liquids and particle size for dry powders are very important to achieve a therapeutic effect. Furthermore, positive pressure MDIs effectively "blow" the medication into the nasopharynx with a high fraction of the dose adhering to the mucosal wall of the mouth and upper airway. Accordingly, the medication does not reach the lungs.

With the advent of resistant bacterial organisms, the improvements in treatment of diseases with high morbidity, such as idiopathic and or primary pulmonary hypertension, cystic fibrosis, persistent primary pulmonary hypertension, and systemic diseases such congestive heart failure with lung involvement, delivery of medications and/or drugs either as small molecules or proteins or peptides or polysaccharides or mucopolysaccharides is important. The aerosol drug delivery method offers advantages over the oral route of administration. Many highly effective agents such as those mentioned above cannot be given orally due to their acid labile properties; or because they are poorly tolerated when given by the intramuscular route. The intravenous route requires hospital care or attentive outpatient care and should be used only by nurses or those skilled or schooled. Pulmonary drug delivery is needed because it could be safe and effective if doses can be controlled and delivered properly.

The diseases where topical administration to the lung is associated with a more positive therapeutic outcome or therapeutic benefit include pneumonia, tuberculosis and cystic fibrosis where there is excessive mucous clogging the passages or bronchioles of the lung. For cystic fibrosis, where there is excess mucous clogging the airways or bronchioles of the lung, direct pulmonary treatment is the most effective therapy.

For aerosol drug delivery, therapies can be viewed simply and naively as topical therapy, but when droplet size is well-controlled and its distribution is homogenous, it can be improved to treat diseases requiring deep lung and/or alveolar targeted delivery. In the present case, deep lung delivery refers to penetration into the small airways of the lung typically ranging between 2-4 microns in diameter. For targeted alveolar drug delivery, droplets should be less than 2 microns, and preferably, less than about 1.1 microns but above 0.5 microns. In each case, the lung should be equally affected with no "dead" spots upon scanning or "clumping" in the larger bronchioles. The device ideally should deliver an even intra-pulmonary distribution of the medication.

For aerosol drug delivery, especially for deep lung or targeted alveoladelivery, it would be beneficial to provide a multi-use, refillable, and re-useable portable aerosol inhalation device that targets the deep lung and alveolar surfaces and that can be used outside of a medical facility, at home or under supervision in a chronic care facility, such as a nursing home. Further, the device should filter the exhaled air and have low residual volumes to prevent contamination or inadvertent exposure, especially with antibiotics, since many people and caregivers have circulating antibodies and can experience an allergic reaction to such chemicals; typically this is seen with penicillin. Still further, the device should have unique ports for placing the medication into an aerosolizing chamber, with minimal loss or inadvertent exposure, more than once and for the device to allow disassembling for cleaning when required and re-use.

SUMMARY OF THE INVENTION

This Summary is provided to introduce a selection of concepts in a simplified form that is further described below in the Detailed Description. This Summary is not intended to identify all key features or all essential features of the claimed subject matter, nor is it intended to be used to limit the scope of the claimed subject matter.

In one embodiment, the present invention is an aerosol inhalation device assembly for therapeutic use for deep lung alveolar aerosol targeted drug delivery and includes a nebulizer for generating an aerosol containing droplets of an aqueous and non-aqueous liquid. The nebulizer has a pressurized gas inlet, a nebulizer outlet, and a longitudinal axis extending between the pressurized gas inlet and the nebulizer outlet. An inhalation chamber is in fluid communication with the nebulizer outlet. The inhalation chamber is defined by at least one sidewall. The inhalation chamber extends along the longitudinal axis. An inhalation mouthpiece assembly is in fluid communication with the inhalation chamber and extends outwardly from the at least one sidewall of the inhalation chamber. The inhalation mouthpiece assembly extends at an angle relative to the longitudinal axis. A filter assembly is in fluid communication with the inhalation chamber and extends along the longitudinal axis. The filter assembly includes a filter medium. An exit port is in direct fluid communication with the filter assembly and extends along the longitudinal axis.

Further, the present invention provides the aerosol inhalation device described above and a medication supply device containing inhalation medication, the medication supply device having a connector configured to mate only with the aerosol inhalation device. The mated connectors allow for continuous administration of medication without interruption.

Additionally, the present invention provides a method of inhaling a nebulized medication comprising the steps of providing the nebulizer assembly, and the medication supply device described above; connecting the medication supply device to the injection port; injecting a medication from the medication supply device, through the injection port and into the nebulizer; injecting a low pressurized gas such as 50 psi of 20-26% oxygen and room air at a rate of between about 8 and about 12 liters per minute into the pressurized gas inlet, generating an aerosol of the medication, the aerosolized medication traveling from the nebulizer to the inhalation chamber; inhaling the aerosolized medication through the inhalation mouthpiece assembly and simultaneously trapping aerosolized medication not being inhaled in the filter medium; and exhaling through the inhalation mouthpiece assembly, such that exhaled air travels through the inhalation chamber and the filter medium to the exit port for discharge to the atmosphere.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

DETAILED DESCRIPTION

In the drawings, like numerals indicate like elements throughout. Certain terminology is used herein for convenience only and is not to be taken as a limitation on the present invention. The terminology includes the words specifically mentioned, derivatives thereof and words of similar import. As used herein, the term "distal" defines a direction away from a user of the inventive device and the term "proximal" finds a direction closer to the user of the inventive device. Also, unless otherwise defined or used herein, the term "liquid" includes aqueous based solutions, oil based solutions, oil/water mixes, emulsions, suspensions, colloids, and other solutions that use a liquid as a base or ingredient.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Also, the articles "an" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims are intended to identify one or more possible embodiments of the claimed subject matter to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, are recited in a particular sequence with corresponding labeling, unless the claim recitations otherwise imply a particular sequence for implementing some or all of those elements, those elements are not necessarily intended to be limited to being implemented in that particular sequence.

Also for purposes of this description, the terms "couple," "coupling," "coupled," "connect," "connecting," or "connected" refer to any manner known in the art or later developed in which energy is allowed to be transferred between two or more elements, and the interposition of one or more additional elements is contemplated, although not required. Conversely, the terms "directly coupled," "directly connected," etc., imply the absence of such additional elements.

Referring now to FIGS. 1A-3, a nebulizer device 100 according to a first exemplary embodiment of the present invention is shown. Nebulizer device 100 generates an aerosol of an aqueous and/or non-aqueous liquid or powder medication for inhalation by a user. The medication is inhaled so that the medication is deposited in the user's lungs for diffusion into the alveolar and in some cases for quick absorption by the user's body—primarily intended to affect the pulmonary vasculature. Formulations such as aqueous, oils and emulsions can be delivered by the device described herein.

Exemplary medication can be a cardiovascular therapeutic agent, such as, for example, phentolamine, an alpha-1 antagonist and those of the same class including enantiomeric forms; sildenafil or other phosphodiesterase 5 inhibitors including enantiomeric forms; prostaglandins, prostacyclins, and prostanoids, including iloprost; nitrates, or peripherally-acting vasodilator agents such as hydralazine and related congeners, or those agents known to affect nitric oxide formation in vascular smooth muscle; nifedipine and related congeners of the slow channel calcium class or those agents known to affect calcium channels in vascular smooth muscle; and endogenous biologic products such as vasoactive intestinal peptide ("VIP"), glucagon and insulin; a pulmonary agent, such as, for example albuterol, terbutaline, or salmeterol, all classified as beta-adrenergic agonists and their enantiomeric forms; ipratropium, or water soluble anti-cholinergic agents; an endocrine agent, such as, calcitonin; α1 antitrypsin or protease enzymes and or their inhibitors; an anti-infective agent, such as, for example, aztreonam; anti-tuberculosis agents such as streptomycin; macrolide antibiotics such as those of the erythromycin class; and antibiotics such as those of the aminoglycoside class such as tobramycin which has been approved for use by inhalation by the Food and Drug Administration but not with this device; or other suitable medications including but not limited to medications that inhibit prostaglandins and cyclo-oxygenases; mucolytic agents such as acetyl cysteine; anti-inflammatories of the muco polysaccharide class also known as heparin, including those referred to as "low molecular weight heparin".

Figure 1A:
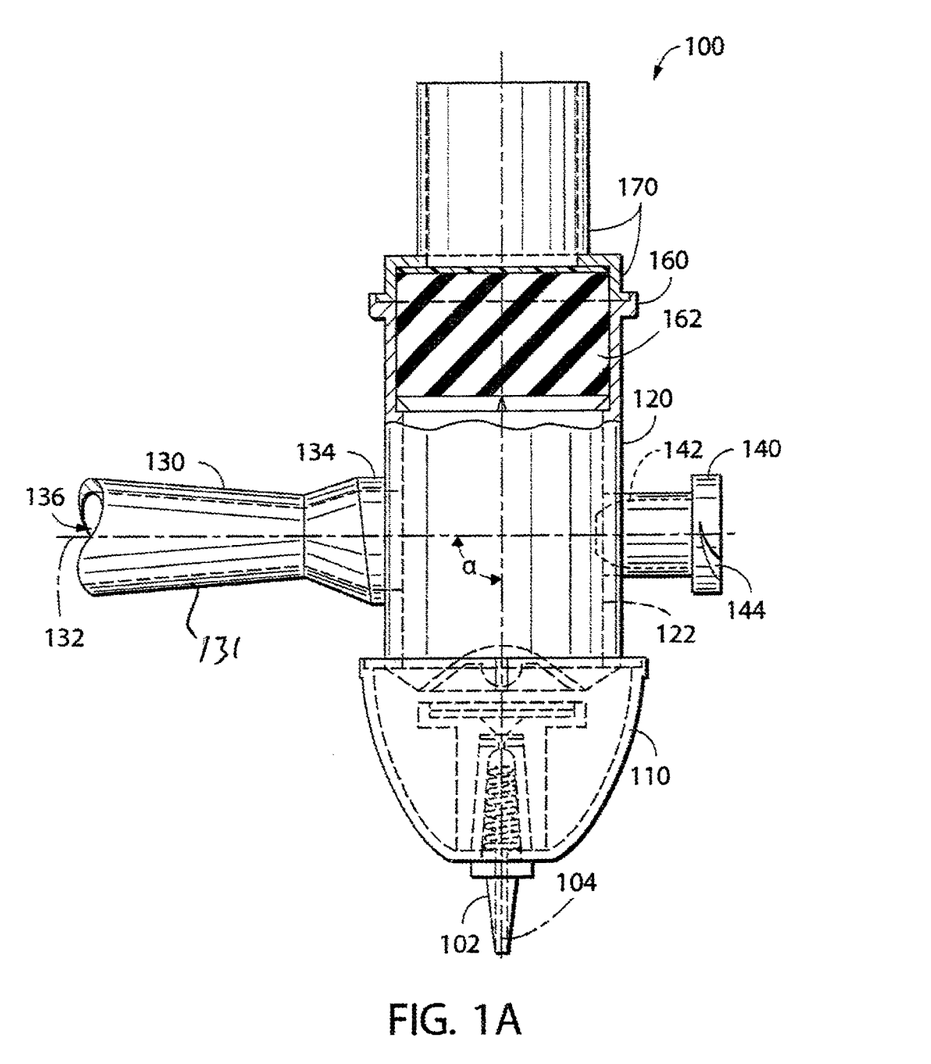
FIG. 1A shows a side elevational view of a nebulizer device according to a first exemplary embodiment of the present invention.
Figure 1B:
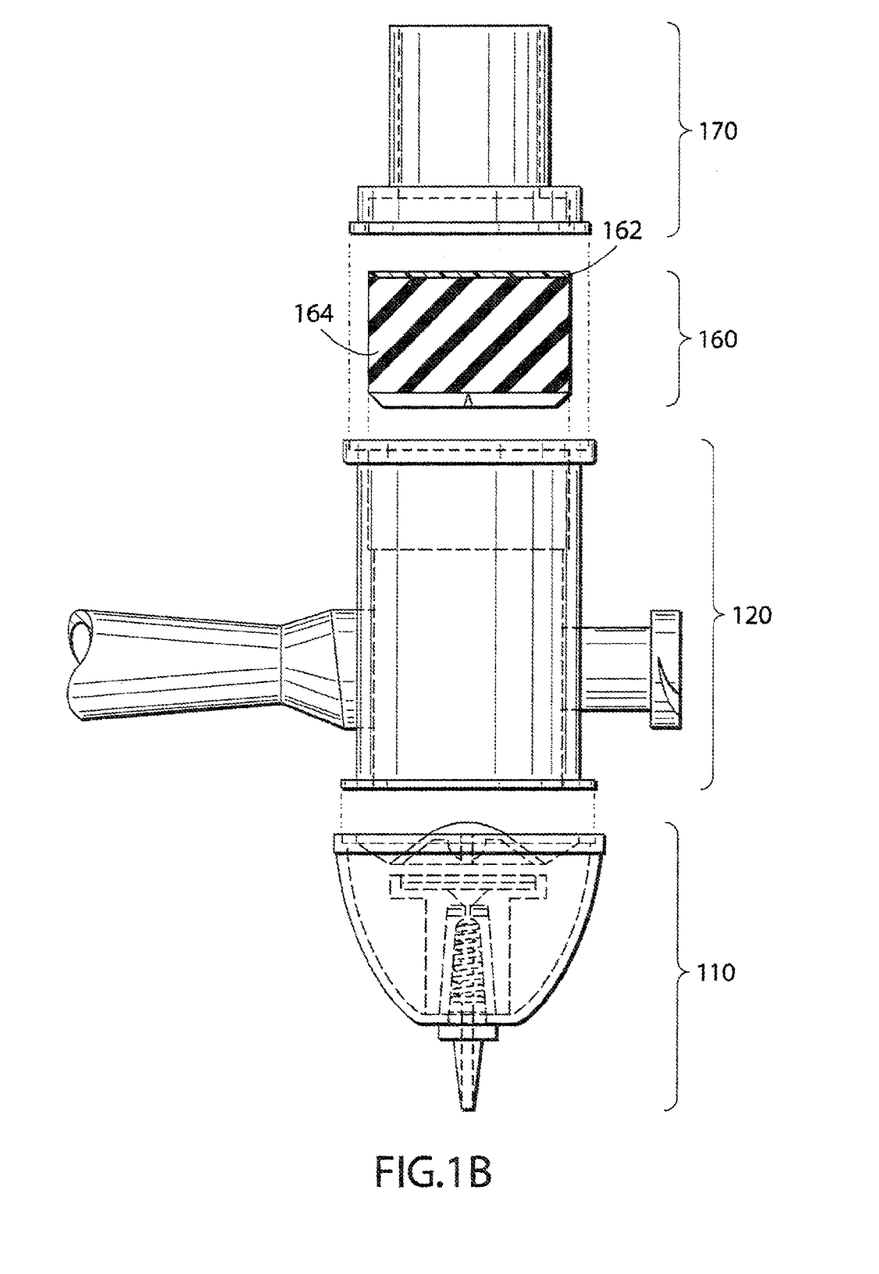
FIG. 1B shows a side elevational view of removable components of the nebulizer device shown FIG. 1A.

Nebulizer device 100 includes a low pressurized gas inlet 102 located at a bottom of nebulizer device 100. A nebulizer 110 is in fluid communication with gas inlet 102. Pressurized gas from gas inlet 102 flows through nebulizer 110 and nebulizes the medication inside nebulizer 110 for inhalation by the user. Liquid medications can be in the form of particle containing fluids, including oils, water-based liquids, and colloidal systems including nano-emulsions or micro-emulsions, and liposomes.

An exemplary nebulizer 110 can be a swirling nebulizer, such as, for example, the SWIRLER®, manufactured by Amici, Inc. of Spring City, Pa., or any of the nebulizer technologies disclosed in U.S. Pat. No. 5,603,314, issued on Feb. 18, 1997, U.S. Pat. No. 5,611,332, issued on Mar. 18, 1997, and U.S. Pat. No. 5,630,409, issued on May 20, 1997, although those skilled in the art will recognize that other types of nebulizers can be used without departing from the scope of the present invention.

In an exemplary embodiment, nebulizer 110 can generate aerosol particles having a mean droplet size of about 2.4 microns. In an alternative exemplary embodiment, nebulizer 110 can generate aerosol particles having a mean droplet size of about 1.4 microns. In still another alternative exemplary embodiment, nebulizer 110 can generate aerosol droplet or liquefied particle having a mean droplet size of about 0.7 microns. In yet another exemplary embodiment, about 80% of aerosolized droplets generated by nebulizer 110 have a diameter of about 1 micron or less.

In another embodiment, nebulizer 110 is able to generate particle sizes in a range of between about 1 micron and about 2.4 microns. Further, the efficiency of nebulizer 110 generates numerous small particles that are suitable for alveolar inhalation. The small size of the nebulized particles, in combination with the large amount, combines to form high level of obscuration within an inhalation chamber 120. By way of example, obscuration can be thought of as being the opposite of the transmittance, with the percentage of obscuration added to the percentage of transmittance being equal to 100 percent.

Obscuration is a relative measurement of the light lost relative to the intensity of light emitted and can be measured by the amount of light (in photons) hitting a detector from a light source. The obscuration can also be an indication of the concentration of a nebulized sample because the more particles or the more volume is taken by the sample, the less photons will make it to the detectors. Obscuration can be viewed as "payload" of the active ingredient. While the obscuration feature is known, obscuration is typically associated with non-pressurized nasal spray in the treatment of allergic rhinitis.

By way of comparative example, for nasal sprays, droplets are larger than 10 microns and obscuration should be high. For deep lung delivery, however, a droplet size of 10 microns would not penetrate or be carried down into the bronchial wall. For nebulizer device 100, high obscuration (>25% as measured by a Malvern Instrument SprayTec or equivalent) can be associated with small droplets size where about >75% of the droplets are below about 1 micron under low pressure (less than about 50 psi). The pressure insensitivity of the droplet/size obscuration relationship is important because now medications could be given effectively to patients with intake restrictive bronchiole obstructive diseases or where there is increased pulmonary bronchial resistance due to excessive mucous. Also but more importantly, the low-pressure delivery prevents or reduces the amount of drug adhering to the nasopharynx preventing lung penetration.

Figure 4:
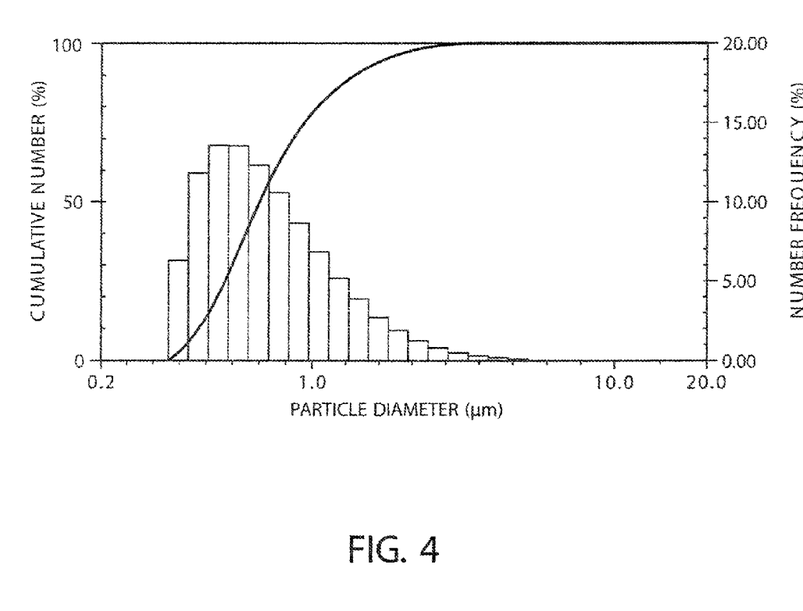
FIG. 4 shows an exemplary graph of average particle size distribution according to a first exemplary embodiment of a nebulizer used with the nebulizer device according to the present invention.

In an exemplary embodiment, a nebulized fluid has an obscuration value of greater than about 25 and, in a further exemplary embodiment, between about 36.7 and about 42, with about 10% of the nebulized particles having a diameter of about 0.41 microns or less; about 50% of the nebulized particles having a diameter of about 0.65 microns or less; and about 90% of the nebulized particles having a diameter of about 1.4 microns or less. The narrow distribution and homogeneity of droplet size is an attribute of this method of aerosolizing. If the distribution of droplet size was "wide" or extended in a "multiple of the mean value", then deep lung therapy or alveolar delivery could not be achieved; the dose to the target site of action would be lower and imprecise. Such "narrow" or homogeneous distribution patterns to the degree described herein have only been seen for nebulizer based methods using a nebulizer similar to nebulizer 110 and not for other non-sonically based nebulizers. See FIG. 4, which shows an exemplary graph of average particle size distribution according to nebulizer 110. The steep slope of the sigmoid curve is an indication of the homogeneity of the droplet sizes.

In still another embodiment, nebulizer 110 is able to generate particles wherein less than about 10 percent of the generated droplets have a diameter of less than about 1.0 microns and less than about 10 percent of the generated droplets have a diameter of greater than about 1.4 microns, meaning that about 80 percent of the generated particles have a diameter between about 1.0 microns and about 1.4 microns. The lower value of about 1.0 microns is important because droplets smaller than about 1.0 microns, and typically, less than about 0.5 microns, tend to be not absorbed by the lungs during inhalation, but instead are exhaled from the patient while particles greater than about 1.4 microns are too large to reach the alveoli.

The relationship between droplet size (between about 1.0 microns and about 1.4 microns) and obscuration (above 36.7) are ideal parameters for deep lung delivery and alveolar target delivery of drugs or biologics or antibiotics where either local or systemic treatment is required.

Inhalation chamber 120 is located vertically above and in fluid communication with nebulizer 110, coaxially along a longitudinal axis 104 with air inlet 102 and nebulizer 110. Inhalation chamber 120 is formed from at least one sidewall 122. As shown in the figures, inhalation chamber 120 has a generally tubular configuration, although those skilled in the art will recognize that inhalation chamber 120 can have other configurations as well. Further, inhalation chamber 120 has only a first (vertical) exit to an exit port 170 and a second (side) exit to an inhalation mouthpiece connector 130. Exit port 170 is generally "blocked" by a filter assembly 160 such that, in the absence of the user exhaling through inhalation mouthpiece connector 130, nebulized liquid from nebulizer 110 can only directly travel from inhalation chamber 120 to inhalation mouthpiece connector 130. This is in contrast to the device disclosed in U.S. Pat. No. 6,412,481, which also includes a corrugated conduit 114 opposite from a mouthpiece 124 that can fill with aerosolized liquid, lowering the density and, thus, the obscuration of the aerosolized liquid in the device, resulting in lower dosages of medication to a patient. Because, with present device 100, the nebulized liquid can only travel to inhalation mouthpiece connector 130, the nebulized liquid cannot be dispersed to other locations, resulting in the higher obscuration values discussed above.

The intake gas can be from a pressurized system or portable nebulizer compressor commonly found in hospitals or nursing homes or medical devices suppliers where a prescription can be written, but it can also be supplied by hand, such as, for example, in the squeezing repeatedly of a manual resuscitation bag.

While, in an exemplary embodiment, the inhalation chamber 120 is fixedly connected to nebulizer 110, such as, for example, by sonic welding, those skilled in the art will recognize that major elements of nebulizer device 100 can be releasably connected to adjacent elements such that elements can be removed for replacement and/or cleaning. As shown, for example, in FIG. 1B, inhalation chamber 120 can be releasably connected to nebulizer 110, such as, for example, by a threaded connection. Such a threaded connection permits nebulizer 110 to be cleaned between uses.

Figure 2:
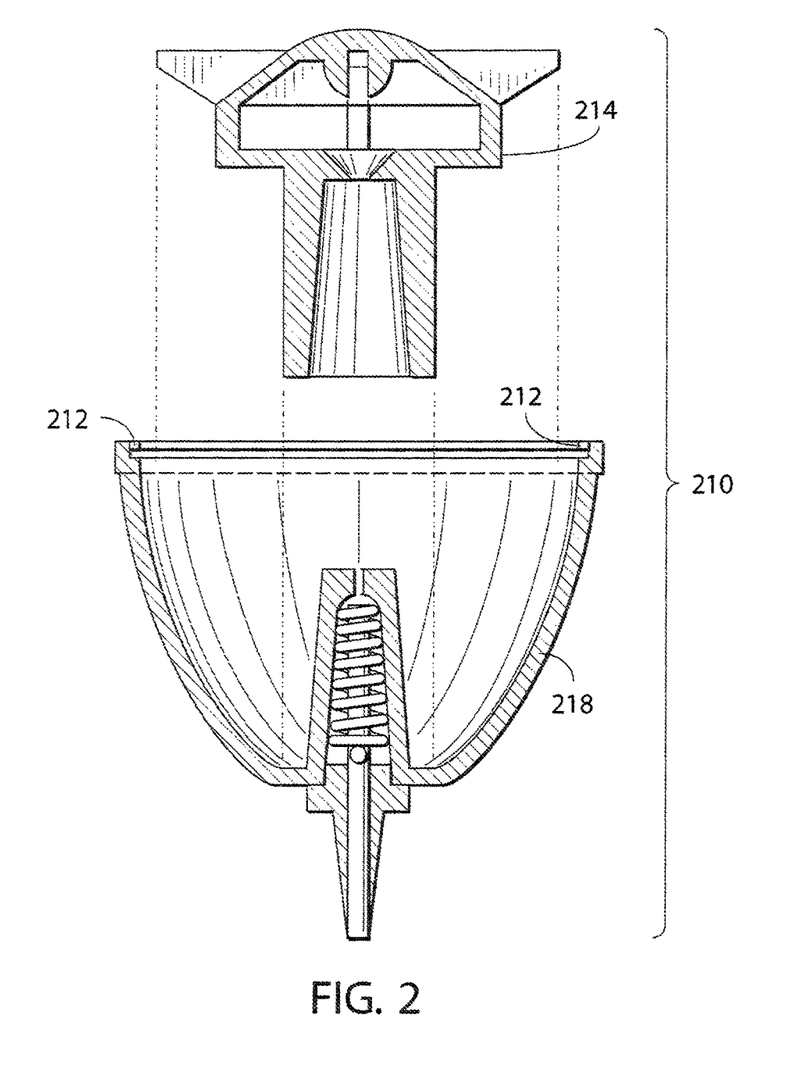
FIG. 2 shows an enlarged exploded view, in section, of an alternative exemplary nebulizer used in the nebulizer device of the present invention.

In an alternative embodiment of a nebulizer 210, shown in FIG. 2, nebulizer 210 includes female threaded connection 212 that can be releasably connected to a mating male connection (not shown) on inhalation chamber 120 and a deflector dome 214 of nebulizer 210 can be releasably removable from the interior of bowl 218 for further cleaning. Such cleaning ability allows for re-use of nebulizer 210.

Referring back to FIG. 1A, in an exemplary embodiment, the interior wall of inhalation chamber 120 is constructed from a material, such as, for example, a hydrophobic material that has a low surface tension such that any nebulized medication that may hit the interior wall tends to vertically slide down the wall and back into nebulizer 110 for re-nebulization. By way of example only, a material that has a surface tension of less than about 40 dynes/cm and, preferably less than about 32 dynes/cm and can be used. Hydrophobic polymers, ceramics, cellulosic and metallic materials, or other materials that have been coated to be hydrophobic can be used as well. Suitable materials can include polyethylene, polypropylene, four carbons, silicones, and the like. An exemplary material is Exact Resin No. 4024, manufactured by Exxon.

Inhalation mouthpiece connector 130 comprises a single hollow tube 131 that extends outwardly from and is in fluid communication with inhalation chamber 120. Inhalation mouthpiece connector 130 extends along an axis 132 with respect to axis 104. Mouthpiece connector 130 can be a "universal" mouthpiece connector that allows for connection of various patient connection media, such as, for example, a mouthpiece, a facemask, endotracheal tubes, and other such devices.

In an exemplary embodiment, axis 132 extends at an angle α generally perpendicularly (about 90°) with respect to axis 104, although those skilled in the art will recognize that axis 132 can extend at an oblique angle relative to axis 104. Mouthpiece connector 130 can be sized for adult use. Alternatively, mouthpiece connector 130 can be reduced in size for pediatric use.

Inhalation mouthpiece connector 130 is a generally single hollow tube having a distal first end 134 connected to inhalation chamber 120 and a proximal second end 136 that is adapted to fit into a user's mouth. In an exemplary embodiment, a length of tube 131 between first end 134 at inhalation chamber 120 and second end 136 is not more than about 2 inches, with a diameter of about ¾ inches. In an exemplary embodiment, mouthpiece connector 130 is fixedly connected to inhalation chamber 120. Alternatively, mouthpiece connector 130 can be removably connected to inhalation chamber 120, such that another mouthpiece or other proximal fitting can be connected to inhalation chamber 120. Unlike some prior art inhalation devices, such as, for example, the aerosol inhalation device disclosed in U.S. Pat. No. 5,603,314, inhalation mouthpiece connector 130 and the path from inhalation chamber 120 to second end 136 of tube 131 notably has an absence of any valves, bends, or other obstructions or tortuous paths therein. The inventors have learned that, in prior art nebulizer devices, such as, for example, the device disclosed in U.S. Pat. No. 5,603,314 to Bono ("Bono"), after a liquid is aerosolized in nebulizer 10, the aerosolized liquid must then travel upward, where a rain-off return 34 is present. Some of the droplets hit rain-off return 34 and drop off, thereby reducing the volume of aerosolized liquid before even entering aerosol conduit 50. Remaining aerosolized liquid enters aerosol conduit 50 and must pass through a one-way valve 51, where remaining larger droplets hit valve 51 and drop off, thereby further reducing the volume of aerosolized liquid past valve 51 and reducing the obscuration value of the aerosolized liquid. The remaining aerosolized liquid must continue through aerosol conduit 50, making several bends, including a 90 degree bend at fitting 60. The bends generate an amount of turbulence that forces some of the aerosolized liquid to hit the walls of aerosol conduit 50 and fitting 60 and drop off as well, even further reducing the obscuration value of the aerosolized liquid.

In contrast, with the inventive assembly of the present application, by way of example only, liquid is aerosolized by nebulizer 110, which generates the same type of aerosolized liquid as nebulizer 10 in Bono. It is after nebulizer 110 where advances provided by the present invention can be realized.

After nebulization by nebulizer 110, the aerosolized liquid travels to inhalation chamber 120, and then follows a relatively short, straight line path (about 2 inches) along longitudinal axis 104 without any obstructions or turns whatsoever, to inhalation mouthpiece assembly 130, which comprises a single conduit hollow tube 131 extending along longitudinal axis 104, to an inhalation mouthpiece (not shown), where the aerosolized liquid is inhaled by the user. The straight, unobstructed line results in a shorter path between nebulizer 110 and the user, resulting in higher obscuration values than could be previously achieved.

Therefore, as the inventors believe, the reduction of tortuosity and the absence of obstructions provided by the structure of the device retains the density of aerosolized liquid per volume inside nebulizer device 100, specifically at second end 136 of tube 131, resulting in higher obscuration values than were able to be previously achieved, even with the same nebulizer (such as the SWIRLER®"), particularly compared to nebulization devices that provided obstructions such as one-way valves and tortuous paths, such as that disclosed in Bono. Further, the single hollow tube that acts as both an inhalation and an expiration tube distinguishes over Bono, which discloses an inhalation tube and a separate exhalation tube.

In an exemplary embodiment, inhalation mouthpiece connector 130 has a dead space of less than about 20 cubic centimeters. In an alternative exemplary embodiment, inhalation mouthpiece connector 130 has a dead space of less than about 10 cubic centimeters. In an alternative exemplary embodiment, inhalation mouthpiece connector 130 has a dead space of less than about 3.8 cubic centimeters. As used herein, the term, "dead space" is the space within inhalation mouthpiece connector 130 between first end 134 at inhalation chamber 120 and second end 136. The dead space is volume within device 100 in which aerosolized medication is not inhaled into the patient during a breath. Between inhalation and exhalation, nebulizer 110 still generates aerosolized medication, which travels through inhalation chamber 120 and into the dead space. But, because the patient is not inhaling at this time the aerosolized medication does not get inhaled. As the patient exhales, the medication is blown out of the dead space back into inhalation chamber 120 and does not have the opportunity to be inhaled by the patient.

Minimizing the size of the dead space therefore minimizes dilution of the medication in mouthpiece connector 130 and, consequently, improves the accuracy of dose delivery, maximizes the concentration of the medication dose, and allows a lower amount of the medication to be required to be in nebulizer 110 in order to deliver a pharmaceutically acceptable amount of the medication to the patient.

First end 134 generally tapers from a larger to a smaller diameter in the distal to proximal direction. Second end 136 has a generally oval cross-section to assist a user's mouth in sealing around the exterior of the second end 136 during use.

While it is desired to use inhalation mouthpiece connector 130 in order to inhale the aerosolized medication from nebulizer device 100, it may not always be practical to use a mouthpiece, such as, for example, for an infant. In such situations, a mask (not shown) can be coupled to the end of inhalation mouthpiece connector 130 and placed over the user's face. In order to prevent nasal inhalation, which can inadvertently filter some of the medication, a nose clip (not shown) can be clamped over the user's nose, thereby forcing the user to inhale through his/her mouth so that the aerosolized medication is more readily administered to the lungs. Alternatively, with mouthpiece connector 130 removed from device 100, device 100 can be directly coupled to a tracheotomy tube or a ventilator for direct inhalation into the patient, A medication injection port 140 extends outwardly from inhalation chamber 120. Injection port 140 can extend about 180° around inhalation chamber 120 from inhalation mouthpiece connector 130. Those skilled in the art, however, will recognize that injection port 140 can extend from inhalation chamber 120 at other locations.

Medication injection port 140 includes a one-way valve 142 that extends into inhalation chamber 120. One-way valve 142 allows an aqueous and/or non-aqueous liquid to be injected into inhalation chamber 120 that prevents the flow of any fluid outwardly from inhalation chamber 120.

A connector 144, such as, for example, a Luer connector, extends outwardly from injection port 140 and is in fluid communication with one-way valve 142. Connector 144 is a non-standard connector, such as, for example, a left-hand threaded Luer connection, in order to prevent inadvertent connection of standard syringes with connector 144, thereby allowing the introduction of potentially undesired and possibly harmful medications into nebulizer device 100. As shown FIG. 1A, connector 144 can extend coaxially with axis 132. Alternatively, connector 144 can extend below axis 132 and/or at an angle oblique to axis 132.

Optionally, as shown in FIG. 2, aqueous and/or non-aqueous liquid and/or solid medicine 201 can be relatively sterilely introduced to device 100 via a pre-loaded syringe 200 or other medication supply device. Syringe 200 has a connector 202 that can only mate with connector 144 on nebulizer device 100. This connector 202-to-connector 144 mating is analogous to a lock and key in which only the appropriate connector 144 properly connects to connector 202. This limitation restricts the ability to use inadvertently syringe 200 in other devices as well as to prevent other devices from being inadvertently connected to connector 144.

In an exemplary embodiment, syringe 200 contains only a sufficient amount of medication 201 for a single application. Such a feature allows syringe 200 to be discarded after medication 201 is transferred from syringe 200 to nebulizer device 100 and also to prevent inadvertent over-medication via syringe 200.

Figure 3:
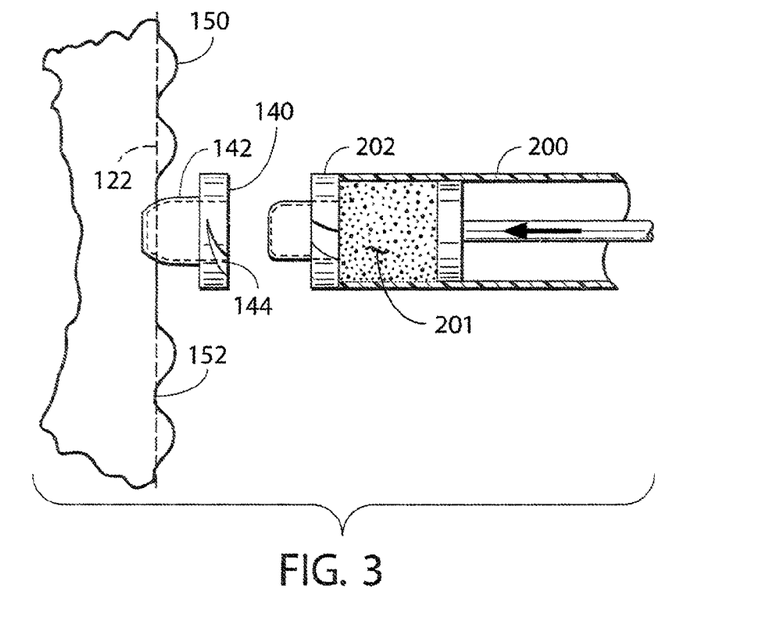
FIG. 3 shows an enlarged view of a connector portion of the nebulizer device shown in FIG. 1A, with a syringe adapted to be connected to the nebulizer device.

Connector 144 allows for dose individualization, such that standard size doses can be adjusted or diluted to adjust to the patient's response or reaction to or for the medication. Additionally, nebulizer 110 is refillable without compromising sterility via connector 144. By adjusting a standard sized dose, the doses can be individualized for a specific patient's needs. By way of example only, an application of medication via connector 144 is 5 ml containing 100 mcg (15 mcg/mL) of VIP or avipdatil. The patient's blood pressure can be monitored during the inhalation process. If the medication dose is too large and the blood pressure falls too low, the patient's inhalation of the medication can be briefly stopped, but the treatment can continue because the remaining volume in the nebulizer 110 can be used to dilute the medication by just adding diluent (i.e., sterilize water, saline, etc.) and thereby reducing the aerosolized concentration from 20 mcg/mL to the desired lower concentration. In an exemplary embodiment, such dilution can be especially useful for short acting drugs, which are those typically lasting less than about 2 to 3 hours. Connector 144 allows for subsequent connections of syringe 200 with additional medicine 201, allowing device 100 to be refilled as needed during treatment. By way of example only, nebulizer 110 can be refilled every several hours, as needed.

The usefulness of dose dilution attribution can be seen also in comparing doses that are useful in children with those that are useful in adults. Adults require higher doses than children. The use of device 100 in the pediatric population would only require a change in mouthpiece connector 130 and a diluted dose of medication to achieve a therapeutic effect. No other changes are required in order to treat pediatric patients.

Alternatively, instead of connecting syringe 200 to connector 144, a continuous or intermittent feed device (not shown), such as, for example, an intravenous bag and drip line, particularly for application of short-acting drugs for continuous treatment over the course of several days, can be connected to connector 144 as long as such continuous feed device has the "lock and key" configuration to mate properly to connector 144. Such a device allows the application of larger volumes (i.e., greater than about 9 mL) than can be stored within nebulizer 110, as well as for longer durations of treatment (i.e., greater than one half hour).

Short acting drugs like VIP and related peptides, aviptadil, phentolamine or sildenafil are ideal for device 100 because such medications require continuous flow or longer than one puffing or inhalation session and such drugs are so active that the volume of each drug needs to be individualized for the particular patient. Again, this would apply to drugs with short half-lives and a short duration of action such as VIP and sildenafil. The inventors note that Aviptadil is not presently approved for oral inhalation by the U.S. Food and Drug Administration ("FDA"). The present device and method of using the device with Aviptadil are contemplated only after FDA approval.

Still alternatively, instead of using connector 144 to inject the medication into device 100, connector 144 can be eliminated and device 100 can be pre-filled with a therapeutically sufficient amount of the medication. In essence, pre-filling device 100 with the medication makes device 100 a single use device. This feature has the benefit of ensuring delivery of the medication into device 100 without inadvertent contamination of the medication via the external environment.

Optionally, first and second finger grips 150, 152 can be formed in or located on inhalation chamber 120. The first finger grip 150 can be located vertically above medication injection port 140, while second finger grip 152 can be located vertically below medication injection port 140. Finger grips 150, 152 are contoured to provide a comfortable mechanism for the user to grasp and hold nebulizer device 100 during use.

Referring back to FIG. 1A, a filter assembly 160 is located vertically above and is in fluid communication with inhalation chamber 120 and extends along longitudinal axis 104. Filter assembly 160 includes a filter medium 162 and a heat and moisture exchange ("HME") filter 164 that are used to trap and return non-inhaled aerosol particles of medication to nebulizer 110 for re-nebulization and inhalation.

In an exemplary embodiment, filter medium 162 can be a product manufactured by 3M under the trademark FILTRETE, although those skilled in the art will recognize that other filter media can be used. Further, as shown FIG. 1B, filter medium 162 and HME filter 164 can both be removed from filter assembly 160 and replaced with a replacement filter medium 162 and/or HME filter 164.

Optionally, filter medium 162 is electrostatically charged to enhance the recovery of non-inhaled medication. Filter medium 162 can be electrostatically charged to a charge density within the range of between about 10 and about 125 nano-Coulombs per square centimeter ("$nC/cm^2$"), or at least about 50 $nC/cm^2$ and preferably about 75 $nC/cm^2$. Filter medium 162 can be a hydrophobic material.

An exit port 170 is in direct fluid communication with filter assembly 160 and extends along longitudinal axis 104. Exit port 170 allows exhaled air from the user to exit nebulizer device 100. Additionally, exit port 170 allows inhaled air to pass through exit port 170 and filter assembly 160 into inhalation chamber 120 for inhalation by the user. Exit port 170 is sized to allow connection of a respiratory resuscitation bag or, alternatively, an external ventilator connection.

The vertical nature of device 100 is deliberate and by design because testing of the relationship between droplet size and obscuration can be altered by airflow path. Those skilled in the art may recognize this notion to be understood that the nature or the degree of droplet size homogeneity and obscuration may depend, in addition to the straight line, non-obscured path from inhalation chamber 120 to second end 136 of tube 131, but also on a non-angled path to the exit ports. If exit port 170 is angled with respect to longitudinal axis 104, then the "pairing" of low droplet size and obscuration value, as discussed above, may change.

As shown in FIG. 1B, exit port 170 can be releasably coupled to inhalation chamber 120, such that exit port 170 can be removed from inhalation chamber 120 for access to filter assembly 160. Exit port 170 can be releasably coupled to inhalation chamber 120, such as, for example, by a threaded connection.

In use, nebulizer device 100 is held such that gas inlet 102 is at the bottom of nebulizer device 100 and exit port 170 is at the top of nebulizer device 100. Connector 202 on syringe 200 is connected to connector 144 on injection port 140 and medication in syringe 200 is injected through injection port 140, and into inhalation chamber 120, where the medication falls via gravity into nebulizer device 100.

A pressurized gas supply is connected to the pressurized gas inlet 102 at the bottom of nebulizer device 100. In an exemplary embodiment, the pressurized gas supply can be air. Alternatively, the pressurized gas supply can be another gas, such as, for example, oxygen, or other biocompatible gas.

The pressurized gas enters nebulizer 110 and mixes with the medication, generating an aerosol of medication. The user places his/her lips around the proximal end 136 of mouthpiece connector 130 and inhales, drawing atmospheric air through exit port 170 and filter assembly 160, into inhalation chamber 120 and through mouthpiece connector 130 and into the user's lungs. As the inhaled air passes through inhalation chamber 120, the aerosolized medication in inhalation chamber 120 is inhaled as well.

The user exhales through mouthpiece connector 130 and the exhaled air passes through inhalation chamber and filter assembly 160 and exits through exit port 170. Any medication in that flow path is caught by filter assembly 160, so that the medication does not exit through exit port 170. The electrostatic charge of filter assembly 160 encourages agglomeration of the medication, forming particles large enough to drop via gravity from filter assembly 160, through inhalation chamber 120, and into nebulizer 110, where the medication is re-nebulized for inhalation.

The nebulization and inhalation of the medication are repeated until the medication is generally used up or after a predetermined period of time when it is determined that a sufficient amount of the medication has likely been inhaled by the user. The pressurized gas supply is secured before removing the pressurized gas supply from pressurized gas inlet 102.

The present invention, due to its efficiency, provides the ability for a high and therapeutically meaningful amount of the stated dose to reach deep lung bronchioles and the alveolar surfaces in rapid fashion. It is possible to achieve a reduction in the amount of medication required in nebulizer device 100 in order to provoke a therapeutically effective dose-response of the medication. For example, for the drug tobramycin, the present therapeutically effective dose of 300 mg per 5 mL in a prior art device can be dosed at 300 mg per 5 mL or alternatively reduced to less than less than 300 mg per 5 mL, alternatively less than 250 mg per 5 mL, and alternatively less than 200 mg per 5 mL, and still alternatively less than 150 mg per 5 mL using nebulizer device 100. Tobramycin can also be provided by continuous uninterrupted therapy, as in a slow continuous infusion (vs. intermittent use). Tobramycin can therefore be administered via device 100 and a continuous rate of between about 40 mg per hour and about 50 mg per hour.

Other drugs can also be provided by continuous therapy. Continuous therapy can be very important for short acting drugs like VIP cogeners, VIP itself, Aviptadil, Sildenafil, Iloprost, or other short-acting medications.

For the drug aztreonam, a short-acting antibiotic, the present therapeutically effective dose of 75 mg per 1 mL in a prior art device can be dosed at 75 mg per 1 mL or alternatively reduced to less than 75 mg per 1 mL, alternatively, less than 50 mg per 1 mL, and alternatively, to less than 40 mg per 1 mL using nebulizer device 100.

For the drug colistin, the present therapeutically effective dose of at least one million units can be dosed at 1 million units or alternatively reduced to less than 1 million units, alternatively, to less than 750,000 units, and still alternatively, to less than 500,000 units using nebulizer device 100.

For the drug albuterol, the present therapeutically effective dose of 1.25 mg per 3 mL can be dosed at 1.25 mg per 3 ml or alternatively reduced to less than 1.25 mg per 3 mL, alternatively, less than 1 mg per 3 mL and alternatively, to less than 0.75 mg per 3 m.

For the drug alpha-1 proteinase inhibitor (API), the present therapeutically effective dose of at least 100 mg can be dosed at 100 mg or alternatively reduced to less than 100 mg, alternatively, to less than 75 mg, and still alternatively, to less than 50 mg using nebulizer device 100.

For the drug iloprost, the present therapeutically effective dose of 5 mcg can be dosed at 5 mcg or alternatively reduced to less than 5 mcg, alternatively, less than 4 mcg and alternatively, less than 3 mcg using nebulizer device 100.

For the drug sildenafil, the present therapeutically effective dose of at least 10 mg can be dosed at 10 mg or alternatively reduced to less than 10 mg, alternatively, less than 7.5 mg and alternatively, less than 5 mg using nebulizer device 100.

For the drug vasoactive intestinal peptide (VIP) or like congeners or peptides, the present therapeutically effective dose of at least 1 mcg can be dosed at 1 mcg or alternatively can be reduced to less than 1 mcg, alternatively, less than 0.75 mcg and alternatively, less than 0.5 mcg using nebulizer device 100.

For the drug insulin, the present therapeutically effective dose of 1 IU per kilogram body weight can be dosed at 1 IU per kilogram body weight or alternatively reduced to less than 1 IU per kilogram body weight, alternatively, less than 0.75 IU per kilogram body weight and alternatively, less than 0.50 IU per kilogram body weight using nebulizer device 100.

The drug examples as illustrated above are for their primary indications. Those skilled in the practice of medicine or in the treatment of the sick, or those trained in pharmacy, know that a drug can have more than one action and because of this attribute, a drug described above be used to treat more than one infectious condition, or varied types of pulmonary or systemic disease requiring different doses than those stated in examples presented above.

The duration of use of nebulizer device 100 in order for a patient to inhale a therapeutically effective dose of medication can be affected by both the flow rate of pressurized gas transmitted to nebulizer device 100 via pressurized gas inlet 102, as well as by the pressure of that gas. In an exemplary embodiment, for a 5 mL dose, the pressurized gas can be at 50 PSI and flowing at a rate of between about 8 and about 12 liters per minute and, in a further exemplary embodiment, about 10 liters per minute. Other exemplary depletion times of the medication are a factor of flow rate, and pressure are shown in the chart below.

| Flow Rate | Depletion time in minutes | | |
|---|---|---|---|
| 8 L per minute | 4.00 | 5.07 | 5.28 |
| 9 L per minute | 3.50 | 4.69 | 4.83 |
| 10 L per minute | 3.16 | 3.33 | 4.16 |
| 11 L per minute | 2.59 | 3.02 | 3.40 |

| Flow Rate | Depletion time in minutes | | |
|---|---|---|---|
| 12 L per minute | 2.38 | 2.90 | 3.23 |
| Pressure | 50 PSI | 45 PSI | 40 PSI |

Where there are concerns about overpressure of the patient lungs, it is noted that the pressures cited above are only required to generate the aerosol and not to pressurize the lungs.

Experimental testing, such as, at the above-listed flow rates and pressures, generated trace residual amounts of fluid within nebulizer 110 due to the extreme efficiency of nebulizer 110. Trace residual amounts of the following fluids, which may be representative of medicines to be nebulized within nebulizer device 100 work: Mazola oil (example of an oil-based liquid, such as a surfactant)—0.002 pounds; 0.65% sodium chloride—0.001 pounds; H2O—0.001 pounds; and non-fat milk (example of micro-emulsion or micro-colloidal system)—0.002 pounds. It is believed that, for a 5 mL aqueous and/or non-aqueous liquid dose within nebulizer 110, over 99% of the aqueous and/or non-aqueous liquid is nebulized over a time frame of less than about 6 minutes. Because of the low residual amounts of the medication retained in device 100 after administering the medication to the patient, a more accurate dosage of the medication is provided to the patient, requiring less medication to be initially provided in nebulizer 110. Also, pre-packaging the medication within nebulizer 110 or injecting the medication into device 100 from syringe 200 reduces the likelihood of contaminating the medication from the exterior environment.

It will be further understood that various changes in the details, materials, and arrangements of the parts which have been described and illustrated in order to explain the nature of this invention may be made by those skilled in the art without departing from the scope of the invention as expressed in the following claims.

We claim:

1. A method of inhaling a nebulized vasoactive intestinal peptide for treating a disease, the method comprising the steps of:
    a. providing a vasoactive intestinal peptide dissolved in a diluent suitable for an aerosol inhalation device in the aerosol inhalation device, the device comprising:
        i. a nebulizer for generating an aerosol containing droplets of a liquid, the nebulizer having a pressurized gas inlet, a nebulizer exit port, and a longitudinal axis extending between the pressurized gas inlet and the nebulizer exit port;
        ii. an inhalation chamber in fluid communication with the nebulizer exit port, the inhalation chamber being defined by at least one sidewall, the inhalation chamber extending along the longitudinal axis;
        iii. at least one finger grip located on the inhalation chamber;
        iv. an inhalation mouthpiece assembly comprising a single hollow tube in fluid communication with and extending outwardly along a linear axis from the at least one sidewall of the inhalation chamber, the inhalation mouthpiece assembly extending at an angle relative to the longitudinal axis;
        v. a filter assembly in fluid communication with the inhalation chamber and extending along the longitudinal axis, the filter assembly including a filter medium; and
        vi. an exit port in direct fluid communication with the filter assembly and extending along the longitudinal axis,
        wherein the nebulizer generates aerosolized vasoactive intestinal peptide;
    b. introducing a pressurized gas into the pressurized gas inlet, generating an aerosol of the vasoactive intestinal peptide, the aerosolized vasoactive intestinal peptide traveling from the nebulizer to the inhalation chamber;
    c. inhaling a portion of the aerosolized vasoactive intestinal peptide through the inhalation mouthpiece assembly and simultaneously trapping a remaining portion of the aerosolized vasoactive intestinal peptide not being inhaled in the filter medium; and
    d. exhaling through the inhalation mouthpiece assembly, such that exhaled air travels through the inhalation chamber and the filter medium to the exit port for discharge to the atmosphere,
    wherein about 90% the aerosolized vasoactive intestinal peptide has a droplet size of about 1.4 microns or less and wherein the obscuration value of the aerosolized vasoactive intestinal peptide is between about 36.7 and about 42.

2. The method according to claim 1, further comprising a step of gravity dropping the trapped remaining portion of the aerosolized vasoactive intestinal peptide from the filter medium, through the inhalation chamber, and to the nebulizer.

3. The method according to claim 1, wherein the inhalation mouthpiece assembly has a dead space of less than about 3.8 cubic centimeters.

4. The method according to claim 1, further comprising performing steps b-d for about 6 minutes and retaining a residual amount having a total weight of less than about 0.45 grams of the vasoactive intestinal peptide dissolved in a diluent in the nebulizer provided in step a.

5. The method according to claim 1, further comprising, prior to step a, diluting the vasoactive intestinal peptide with a liquid diluent to a concentration of between about 15 mcg and about 20 mcg of vasoactive intestinal peptide/ml.

6. The method according to claim 1, wherein providing the vasoactive intestinal peptide comprises providing between about 75 mcg and about 100 mcg of the vasoactive intestinal peptide.

7. The method according to claim 1, wherein providing the vasoactive intestinal peptide comprises providing at least one mcg of the vasoactive intestinal peptide.

8. The method according to claim 1, wherein providing the vasoactive intestinal peptide comprises providing aviptadil.

9. The method according to claim 1, wherein the nebulizer further comprises a medication injection port in fluid communication with the inhalation chamber, the injection port having a one-way valve incorporated therein, wherein the method further comprises delivering the vasoactive intestinal peptide in solution to the nebulizer through the medication injection port.

10. The method according to claim 9, wherein the method further comprises continuously providing the vasoactive intestinal peptide to the nebulizer through the injection port, allowing for continuous inhalation of the vasoactive intestinal peptide through a syringe.

11. The method according to claim 9, wherein the method further comprises continuously providing the vasoactive intestinal peptide to the nebulizer through the injection port from an intravenous drip line, allowing for continuous inhalation of the vasoactive intestinal peptide.

12. The method according to claim 1, wherein the method further comprises flowing a gas through a helical conduit in the nebulizer, thereby increasing the velocity of the gas through the nebulizer and generating a swirling motion of the gas as the gas exits the helical conduit, thereby shearing the dissolved vasoactive intestinal peptide that then strikes a baffle located above the helical conduit, resulting in at least a partial sub-micronic particle distribution.

13. The method according to claim 1, further comprising, after step d, diluting the vasoactive intestinal peptide in the aerosol inhalation device with a diluent and repeating steps a-d.

14. The method according to claim 1, further comprising continuously providing the additional dissolved vasoactive intestinal peptide through the fill connection during an inhalation session.

15. The method according to claim 1, wherein the at least one finger grip comprises a first finger grip located above the fill connection and a second finger grip located below the fill connection, wherein the method further comprises gripping the inhalation device by the at least one finger grip.

16. The method according to claim 1, wherein about 80 percent of the droplets have a diameter between about 1.0 microns and about 1.4 microns.

17. The method according to claim 1, wherein the inhalation mouthpiece has an absence of obstructions therein.

18. The method according to claim 1, wherein the inhalation chamber has only a first exit port to the filter assembly and a second exit port to the inhalation mouthpiece assembly.

* * * * *